United States Patent [19]

Wagner et al.

[11] Patent Number: 4,698,263

[45] Date of Patent: Oct. 6, 1987

[54] SAC HAVING A MARKER LINKED THERETO

[75] Inventors: Daniel B. Wagner, Raleigh, N.C.; Robert A. Baffi, Devaulf, Pa.

[73] Assignee: Becton Dickinson and Company, Franklin Lakes, N.J.

[21] Appl. No.: 737,244

[22] Filed: May 23, 1985

[51] Int. Cl.$^4$ .......................... A61K 9/42; B01J 13/02
[52] U.S. Cl. .................................. 428/402.2; 264/4.1; 264/4.3; 264/4.6; 424/1.1; 424/450; 436/528; 436/546; 436/829
[58] Field of Search ............... 424/38, 450; 428/402.2; 436/829

[56] References Cited

U.S. PATENT DOCUMENTS

| | | | |
|---|---|---|---|
| 4,193,983 | 3/1980 | Ullman et al. | 424/1.1 X |
| 4,224,179 | 9/1980 | Schneider | 264/4.3 |
| 4,235,871 | 11/1980 | Papahadjopoulos et al. | 264/4.6 X |
| 4,283,382 | 8/1981 | Frank et al. | 436/546 X |
| 4,374,120 | 2/1983 | Soini et al. | 424/7.1 X |
| 4,432,907 | 2/1984 | Wieder et al. | 424/7.1 X |
| 4,483,929 | 11/1984 | Szoka | 435/8 X |
| 4,544,545 | 10/1985 | Ryan et al. | 424/7.1 X |

FOREIGN PATENT DOCUMENTS 2089681  6/1982  United Kingdom .

*Primary Examiner*—Richard D. Lovering
*Attorney, Agent, or Firm*—Elliot M. Olstein

[57] ABSTRACT

Vesicles are formed having a detectable marker and ligand conjugated to compounds forming the vesicle wall. The vesicles are dried, and reformed by addition of water for use in an assay.

9 Claims, No Drawings

SAC HAVING A MARKER LINKED THERETO

This invention relates to sacs including a detectable marker, and the use thereof in an assay for an analyte. This invention further relates to sacs including a detectable marker which are sensitized with a ligand and the use thereof in an assay for an analyte.

Sacs, and in particular, lipid vesicles, have been prepared which have a detectable marker encapsulated therein. Such sacs have been employed in assays for a ligand (analyte). In a representative assay, a ligand to be determined (analyte) and tracer comprised of a sac having a detectable marker encapsulated therein, which sac is also sensitized with the analyte or appropriate analog thereof, compete for a limited number of binding sites on a binder for the analyte. The amount of tracer which becomes bound to the binder is inversely proportional to the amount of analyte in the sample. After separating bound and free tracer components, the amount of the bound and/or free tracer is ascertained by determining tte detectable marker in the bound and/or free tracer portion of the sample, which provides a measure of analyte in the sample.

The assay provides for increased sensitivity, and amplification of signal in that the single ligand molecule, which is employed in forming the tracer, includes a plurality of marker components.

In many cases, however, the sacs having the detectable marker encapsulated therein do not possess sufficient stability in that the detectable marker "leaks" from the sacs prior to or during the assay, which limits the effectiveness of such sacs in an assay. The term "leaks", as used herein, means that either the material escapes from an intact sac or the material escapes as a result of destruction of the sac.

In addition, the sac having the marker encapsulated therein must be maintained in water so as to maintain the sac structure. This increases the storage problems associated with sacs including an encapsulated marker.

In accordance with one aspect of the present invention, there is provided a vesicle wherein one or more of the compounds used in forming the wall of the vesicle has a detectable marker attached thereto wherein water is removed to provide a dry composition of sac forming components, a portion of such components having a detectable marker attached thereto which dry composition can be reconstituted with water to provide a vesicle having the detectable marker conjugated thereto.

Applicant has found that if the detectable marker is conjugated to one or more of the compounds used in forming the wall of the vesicle, rather than being encapsulated in the sac, it is not necessary to store the vesicle in water. As a result, the vesicle, including a detectable marker conjugated thereto, may be stored as a dry composition, and prior to use, the composition may be reconstituted in water to provide a vesicle including a detectable marker.

Sacs which have a detectable marker conjugated thereto are produced by derivatizing one or more of the materials which are used in producing the vesicle with the detectable marker. The sac is preferably a vesicle which is produced from one or more amphiphilic compounds, with such vesicles generally being prepared from lipids. When the vesicle includes a lipid, it is often referred to as a liposome; however, as known in the art, vesicles can be produced from amphiphilic compounds which are not lipids.

Thus, for example, as known in the art, liposomes can be prepared from a wide variety of amphiphilic compounds, including phospholipids, glycol lipids, steroids, relatively long chain alkyl esters such as lecithin, fatty amines and the like. A mixture of fatty materials may be employed such as a combination of neutral steroid, a charged amphiphile and a phospholipid.

As illustrative examples of phospholipids there may be mentioned sphingomyelin, dipalmitoyl, lecithin and the like. As representative steroids, there may be mentioned cholesterol, cholestanol, lanosterol, and the like. As representative examples of charged amphiphilic compounds, which generally contain from 12 to 30 carbon atoms, there may be mentioned mono- or dialkyl phosphate ester, quaternary ammonium salts, or ar alkylamine; e.g., dicetyl phosphate, dioctadecyl sulfonate, didodecyl dioctylammonium formide, and the like.

In accordance with a preferred aspect of the present invention, the vesicle is also derivatized with a ligand which is either an antigen, hapten or antibody, whereby the vesicle may be employed as a tracer in an assay for analyte. In acccrdance with this aspect of the invention, the dry composition includes vesicle forming components some of which are derivatized with a ligand and some of which are derivatized with a detectable marker, and when water is added, there is forxed a vesicle which is derivatized with both marker and ligand for use in an assay.

The derivatization of the vesicle with a detectable marker may be accomplished by a wide variety of procedures, and in particular, those procedures previously used for conjugating a ligand to a sac; i.e., the procedures for coupling a ligand to a sac may also be used for coupling a detectable marker to a sac.

The marker and ligand may be conjugated to the sac through a suitable functional group. As representative examples of suitable functional groups, there may be mentioned: carboxylic acid groups, diazotiazable amine groups, succinimide esters, anhydrides, mixed anhydrides, benzimidates, nitrenes, isothiocyanates, azides, sulfonamides, bromoacetamides, iodoacetamides, carbodimides, sulfonylchlorides, hydrazides and thioglycols. Such functional groups may be provided directly on the wall forming material or by substituting the wall forxing material with a suitable spacer group, which includes a functional group for conjugation to the marker or ligand.

The sacs may be coupled to the marker (and also the ligand) by the use of an appropriate coupling or spacer compound (one that does not destroy the immunoreactivity of the ligand). As known in the art, the coupling compound has two reactive functional groups, one of which functional groups is capable of reacting or being linked to a functional group of the ligand portion of the tracer, and the other of which is capable of reacting or being linked to a functional group on the sacs. For example, the spacer or coupling compound, which includes at least two reactive substituent groups, may ccntain either a carboxyl, isocyanate, isothiocyanate, amino, thiol, hydroxy, sulfonyl, carbonyl, etc., substituent group which, as should be apparent, is dependent upon the functional group present in the ligand and sacs which are to be coupled to each other.

Alternatively, the sacs may be coupled directly to the marker or ligand. Thus, for example, if the ligand or marker portion of the tracer has an axino substituent group, and the compound or compounds used in forming the sac has a carbonyl or carboxyl substituent group, then the ligand and sacs may be directly conjugated to each other by procedures known in the art; for example, an active ester technique.

The wall forming material may be derivatized with the marker either before or after forming the sac. In accordance with a preferred embodiment, the wall forming material is derivatized with a marker prior to producing the sac or vesicle.

The sac forming material, which is derivatized with marker as well as any material derivatized with a ligand and the other materials which are used in producing the sac or vesicle may be employed for producing a vesicle by procedures generally known in the art. Thus, for example, a liposome may be prepared by a reverse emulsion technique, as described in U.S. Pat. No. 4,235,871, wherein there is provided a water-in-oil emulsion containing the materials for forming the vesicle, followed by evaporation of the solvent to produce a gel-like mixture which is converted to a vesicle by either agitation or addition of the gel-like mixture to water.

Procedures for producing sacs are generally known in the art, and such procedures may be employed for producing sacs, which are derivatized with a marker (and in some cases also with a ligand) in accordance with the present invention.

The detectable marker which is conjugated to the sac may be one of a wide variety of detectable markers, including but not limited to chromogens (fluorescent materials and/or absorbing dyes), radioactive materials, enzymes, phosphorescent materials, luminescent materials, spin labels, a detectable metal, etc.

The vesicle which is derivatized with a detectable marker, and which may also be derivatized with a ligand, is dried to provide a dry mixture of the vesicle forming components which can be stored in dry form, and added to water prior to use to reform a vesicle derivatized with the marker, and if previously present, the vesicle is also derivatized with the ligand.

Thus, for example, in accordance with this aspect of the invention, a vesicle produced as hereinabove described, whereby the wall forming components, including the amphiphilic chelating agent having the detectable marker complexed thereto may be stored in a dried form for subsequent reforming into a vesicle by addition of water. The drying may be readily accomplished by freeze drying; for example, cooling to −70°C. in dry ice acetone, followed by use of a freeze drying apparatus.

The freeze dried or dried vesicle may then be reformed by addition of water such as a Tris-buffer at pH 8 to produce the vesicle, which includes the detectable marker, as well as any ligand attached to an amphiphilic compound originally used in producing the sac.

As should be apparent, in this manner, it is no longer necessary to store the vesicle in water, which increases the storage stability of the vesicle, and such vesicle may be effectively employed as a tracer in an assay by simply reconstituting the dried materials with water.

In accordance with another aspect of the present invention, the sac or vesicle which has a detectable marker attached thereto is also derivatized with a ligand for use in determining an analyte in a sample, with such derivatized sac, including a detectable marker attached thereto, generally being referred to as a "tracer". The ligand which is employed for derivatizing the sac is either an antibody, antigen or hapten, and the selection of the ligand is dependent upon the analyte to be determined. Thus, for example, if the assay is a competitive assay for determining an antigen or hapten, the ligand employed in producing the tracer is either the analyte or appropriate analog thereof. The term "appropriate analog" means that the analog of the analyte is bound by the binder for the analyte.

If the assay is a "sandwich" type of assay, then the ligand employed in producing the tracer would be a ligand which is specific for the analyte to be assayed; for example, an antibody elicited in response to the antibody or antigen to be assayed. Alternatively, the antibody could be a monoclonal antibody.

The binder which is used in the assay is also dependent upon the analyte. Thus, for example, if the analyte is an antigen or hapten, the binder may be an antibody or a naturally occurring substance which is specific for the analyte. If the analyte is an antibody, the binder may be either an antibody, an antigen or naturally occurring substance which is specific for the analyte.

The binder which is used in the assay may be employed in supported or unsupported form.

The tracer which is produced in accordance with the present invention may be determined in an assay, in most cases, without rupturing the sac or vesicle. More particularly, the marker is generally a hydrophilic material, whereby such detectible marker is external to the bilayer which forms the sac or vesicle. It is to be understood, however, that when the term "external" is employed, with respect to the bilayer of the sac, it is meant that such external component may be inside or outside of the sac and that the external portion of the bilayer is both inside and outside of the sac. Thus, a portion of e marker is on the outside of the sac, rather than inside of the sac and may be detected without rupturing of the sac. It is to be understood, however, that the sac may also be ruptured in order to determine the marker.

The overall procedure for the assay may be as generally practiced in the art with the determination of the detectable marker being accomplished by a procedure suitable for the particular marker employed.

In accordance with one assay procedure, the tracer formed in accordance with the present invention may be employed for determining an analyte in a competitive type of assay wherein the tracer and analyte compete for a limited number of binding sites on a binder for the tracer and analyte. The presence and quantity of analyte in a sample may be determined by detecting the tracer in the bound and/or free portions of the assay; i.e., tracer bound to binder, and tracer which does not bind to the binder. As known in the art, the amount of tracer which becomes bound to the binder is inversely proportional to the amort of analyte in the sample, and the quantity of analyte may be determined by comparing the value obtained in the assay with alues obtained for the assay with known quantities of analyte; i.e., a standard curve.

The assay may be a "sandwich" assay in which case antigen is determined by use of an antibody supported on a solid support and a sac derivatized with both antibody and detectable marker.

As hereinabove indicated, the detectable marker may be determined in some cases without rupturing of the sac, and in other cases the detectable marker is determined by rupturing the sac. The sac may be ruptured by procedures generally known in the art such as use of a detergent, enzymatic lysing, change in conditions of temperature, pH, concentration, etc.

In accordance with a preferred aspect of the invention, the vesicle having a detectable marker conjugated thereto is formed from an amphiphilic chelating agent which is comprised of a hydrophilic chelating protion and a hydrophobic portion. Such amphiphilic chelating agents may be prepared by conjugating or derivatizing a chelating agent with a compound including a hydrophobic moiety of the type generally employed in producing vesicles. Thus, for example, a chelating agent may be derivatized with or conjugated to a phospholipid, such as a phosphatidylethanolamine; a steroid, such as cholesterol; a glycolipid; a long chain dialkylamine; a long chain dialkylcarboxylic acid or ether; an ester of polyhydroxyalcohol, such as glycerol, so as to provide an amphiphilic chelating agent which is exloyed to form a portion of the sac. In such an embodiment, a detectable metal marker is complexed to the chelating agent, and the vesicle may be stored in a dry form and then reconstituted with water.

Any one of a wide variety of chelating agents may be employed for such purpose, and as representative examples of such chelating agents, there may be mentioned aminocarboxylic acids, iminocarboxylic acids, ethers, thiols, phenols, glycols and and alcohols or polyamines, ethylenediaminetetracetates, diethylenetriaminepenta or tetracetates, polyethers, polythiols, cryptands, polyetherphenolates, polyether thiols, ethers of thioglycols or alcohols, polyaminephenols, all either acyclic, macrocyclic, cyclic, macrobicyclic or polycyclic, or other similar ligands which produce highly stable metal chelates or cryptates.

The selection of a particular chelating agent will depend upon the metal to be chelated, as well as the wall forming material to which the chelating agent is to be conjugated.

The chelating agent is conjugated to a compound including a hydrophobic moiety to provide an amphiphilic chelating agent through a suitable functional group. As representative examples of suitable functional groups, there may be mentioned: carboxylic acid groups, diazotiazable amine groups, succinimide esters, anhydrides, mixed anhydrides, benzimidates, nitrenes, isothiocyanates, azides, sulfonamides, bromoacetamides, iodoacetamides, carbodimides, sulfonylchlorides, hydrazides and thioglycols. Such functional groups may be included in the hydrophobic moiety and/or chelating agent to permit direct linkage or the hydrophilic chelating agent may be conjugated to the hydrophobic moiety through a suitable spacer group.

Thus, for example, suitable spacer compounds include diamines, such as hexamethylenediamine; 'diaminocarboxylic acids such as lysine; polyethers; polyalcohols; aminoalcohols; aminopolycarboxylic acids, polycarboxylic acids; polyhydroxycarboxylic acids; hydroxypolycarboxylic acids, etc.

The selection of suitable spacer compounds and functional groups for conjugating a chelating agent to a compound including a hydrophobic moiety to provide an amphiphilic chelating agent suitable for use in producing a vesicle is deemed to be within the scope of those skilled in the art from the teachings herein. A particular preferred type of linkage is an amide linkage formed by conjugating a carboxyl group of a chelating agent to an amino group of a compound including a hydrophobic moiety. For example, such amide linkages may be formed by conventional peptide synthesis methods.

The chelating agents which are particularly preferred are aminocarboxylic acids; and in particular, ethylenediaminetetraacetic acid (EDTA) and diethylenetriaminepentaacetic acid (DTPA). Such chelating agents may be conjugated or derivatized; for example, with a long chain dialkylamine; or with a phosphatidylethanolamine or with a steroid, such as cholesterol or cholestanol to provide an amphiphilic chelating agent suitable for use in forming a vesicle.

As representative examples of preferred amphiphilic chelating agents, there may be mentioned those represented by the following structural formulas:

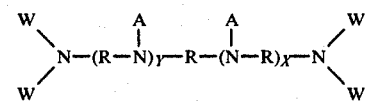

wherein
each R is an alklene group or p-diazoniumphenyl substituted alkylene group wherein the alkylene group has from 2–4 carbon atoms and each R group may be the same or different,
X and Y are integers from 0–8,
A is hydrogen or W;
one W group is

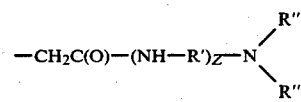

or B—(PO$_4$)—(CH$_2$)$_2$—NH—C(0)—CH$_2$—; or
A$_1$—B$_2$—C(0)—CH$_2$—
wherein R' is an alkylene group having from 2–10 carbon atoms; R" is an aliphatic hydrocarbon having at least 11 carbon atoms and may be the same or different and Z is an integer of from 0–4, and the remaining W groups are —CH$_2$—C(0)—OR'''
wherein R''' is hydrogen, an alkali metal or an amine, and B is

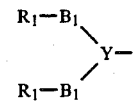

wherein Y is an aliphatic hydrocarbon radical having from 1–5 carbon atoms, preferably 3 or 4 carbon atoms; each of B$_1$ is individually —O—; —C(0)0—; or —CH$_2$—and may be the same or different; and each R$_1$ is a substituted or unsubstituted hydrocarbon radical (saturated or unsaturated) having at least 11 carbon atoms and may be the same or different,
and A$_1$ is cholesterol or cholestanol and B$_2$ is a radical formed from a difunctional spacer compound.

Particularly preferred compounds of this type are a dialkylamine conjugated to ethylenediaminetetraacetic acid or salt thereof (X and Z are zero, R is ethylene); and a dialkylamine conjugated to diethyleneaminepentaacetic acid or salt thereof (R is ethylene, Y is 1, X and Z are zero).

Another preferred compound is one in which W is A$_1$—B$_2$—C(0)—CH$_2$$^-$$_2$,
A$_1$ is a cholesterol radical and $B_2$ is —O—C(O)—NH—$R_3$—NH— wherein $R_3$ is an alkylene radical.

The chelating agent may be conjugated to the compound including a hydrophobic moiety by procedures known in the art. For example, the bis-anhydride of DTPA may be produced by refluxing pyridine and acetic anhydride. The anhydride may be conjugated to an amino group; for example, a long chain dialkylamine by a modification of the procedure reported by Takshita (J.A. C.S. 59 #2 (Feb. 1982) wherein a solution of the anhydride and triethylamine in tetrahydrofuran is reacted with a long chain dialkylamine to produce an amphiphilic chelating agent.

A chelating agent may also be conjugated to cholesterol by use of a spacer compound. For example, diaminohexane and triethylamine dissolved in isopropanol is reacted with a solution of beta cholesterol chloroformate, and the resulting product is conjugated to the bis-anhydride of DTPA by the procedure hereinabove described for conjugating the anhydride to a long chain alkylamine.

Procedures for producing amphiphilic chelating agent are deemed to be within the scope of those skilled in the art from the teachings herein. Procedures for conjugating chelating agents to other compounds are also applicable to providing amphiphilic chelating agents in accordance with the present invention.

The amphiphilic chelating agent forms a portion of the materials used in producing the vesicle. The remaining materials used in forming the vesicle may be of a type known in the art, and include various phospholipids, glycolipids, dialkylphosphates, lecithins, steroids, etc. Compounds which are suitable for producing vesicles are generally known in the art and such compounds may be employed in conjunction with an amphiphilic chelating agent for producing vesicles in accordance with the present invention.

In accordance with a preferred embodiment, a portion of the amphiphilic compound(s) employed for producing the vesicle is derivatized with a ligand whereby the vesicle wall includes a chelating agent and a ligand. In accordance with the preferred embodiment, a detectable metal marker is complexed to the chelating agent, whereby the vesicle may te employed as a tracer in an assay. In accordance with this aspect of the invention, the tracer is comprised of a particle in which both the detectable metal marker and the ligand form part of the particles; however, there is no covalent linkage between the ligand and detectable metal. The detectable metal marker is complexed to an amphiphilic chelating agent, and another aphiphilic compound is derivatized with a ligand to form separate portions of the vesicle wall; however, there is no covalent linkage between the detectable marker and the ligand.

The vesicle wall is formed from a mixture of vesicle wall forming components which include the amphiphilic chelating agent, and in accordance with a preferred embodiment, an amphiphilic compound derivatized with a ligand. The amount of amphiphilic chelating agent employed in producing the vesicle is dependent upon both the amount of the detectable metal marker which is to be complexed to the vesicle, and the ability to provide a vesicle with the desired properties. In most cases, the amphiphilic chelating agent does not exceed 60 mole percent of the components employed in forming the vesicle, and generally does not exceed 50 mole percent. In general, the amphiphilic chelating agent is present in an amount of at least 5 mole percent.

As hereinabove indicated, higher and lower amounts may be employed, and the selection of an optimal amount is deemed to be within the scope of those skilled in the art from teachings herein.

The amphiphilic compound derivatized with a ligand, when included in forming the vesicle, is present in an amount dependent upon the ligand, and the assay in which it is to be employed. As known in the art, sensitivity is increased with lower amounts of ligand. The selection of an optimum amount of ligand is deemed to be within the scope of those skilled in the art from the teachings herein.

Although it may be possible to form a portion of the wall of the vesicle so that it includes an amphiphilic chelating agent after the vesicle has been formed (for example, by derivatizing cholesterol included as a portion of the wall of the vesicle with a chelating agent), the amphiphilic chelating agent is preferably provided prior to producing the vesicle, and the vesicle is initially formed with such amphiphilic chelating agent. Similarly, although it is possible and known to derivatize an amphiphilic compound included in a formed sac with a ligand, it is preferred to produce such an amphiphilic compound derivatized with a ligand, prior to production of the vesicle.

Similarly, although it is possible to add a detectable metal for complexing with the amphiphilic chelating agent of the sac subsequent to formation of the sac, in accordance with a preferred embodiment, the amphiphilic chelating agent is complexed with the detectable metal, prior to production of the vesicle. In general, the metal is chelated to the amphiphilic chelating agent to be employed in producing the sac under conditions such that the chelating portion is ionized, with such ionization generally being accomplished at a pH of 6. After addition of the detectable metal, any detectable metal which is not chelated to the amphiphilic chelating agent, is removed; for example, by the use of gel filtration.

The amphiphilic chelating agent, as well as other materials which are to be used in producing the vesicle (including in accordance with a preferred embodiment an amphiphilic compound derivatized with a ligand) may be formed into a vesicle by procedures generally known in the art. For example, vesicles may be produced in accordance with the type of procedure generally described in U.S. Pat. No. 4,235,871. In accordance with such a procedure, the vesicle wall forming components, including the amphiphilic chelating agent, and in accordance with a preferred embodiment, an amphiphilic compound derivatized with a ligand, in an organic solvent are placed in a flask, and the solvent evaporated to form a film. Subsequently, an aqueous buffer, which contains the metal to be chelated or complexed to the sac, is added to form the sac, followed by sonication. Chelated metal is removed as hereinabove described.

The above procedure and other procedures which are generally suitable for producing vesicles are also suitable for the purposes of the present invention. In accordance with the present invention, the sac or vesicle may be unilamellar or multilamellar. In most cases, a multilamellar sac is employed in that such a vesicle increases the amount of detectable metal which can be incorporated into the sac.

The vesicles produced in accordance with the invention are highly mobile, and in general, the particles have a size in the range of from 0.05 to 10.0 micron, in diameter. The vesicles, by use of the chelating agent in appropriate amounts, are formed with a high ratio of detectable metal atoms per vesicle, whereby there can be obtained an amplification of signal in an assay. Moreover, the vesicles may also be provided with a plurality of ligand molecules, per vesicle.

In most cases, the vesicle includes a steroid component, as well as a glycolipid or phospholipid component, and such lipids may be provided in either neutral form or in acid form.

The production of a suitable vesicle by proceeding in accordance with the present invention should be apparent to those skilled in the art from the teachings herein in that the techniques which are generally applicable for producing vesicles are also applicable to producing vesicles including an amphiphilic chelating agent in accordance with the present invention.

The detectable metals which may be chelated or complexed include radioactive or non-radioactive metals. For example, radioactive metals include radioactive cobalt. In addition, the detectable metal marker may be formed from other than a radioactive metal, such as a material possessing the properties of paramagnetism, fluorescence or phosphorescence.

Rare earth metals of both the actinide and lanthanide series are preferred. As representative examples, there may be mentioned terbium, dysprosium, europium, samarium, and neodimium.

The detectable metal marker is preferably a rare earth metal in that such rare earth metal may be employed as a detectable marker in an assay which relies on fluorescence, and in particular, a time-delay fluorescent assay.

The ligand which is employed in conjunction with the solid particles, and in particular, in conjunction with a vesicle by derivatizing an amphiphilic compound employed in forming the vesicle, may be any one of a wide variety of ligands for which there is a binding partner, sometimes referred to as an anti-ligand. The ligand, in general, is a hapten, antibody, or antigen.

The vesicles which are formed in part from an amphiphilic chelating agent having a detectable metal complexed thereto, and which in accordance with a preferred embodiment, also include an amphiphilic compound, which is derivatized with a ligand, can be provided as a dried mixture of the wall forming components, and such dried mixture can be reconstituted with water to provide a vesicle, which includes the detectable metal marker, all as hereinabove described.

In accordance with a preferred procedure, the tracer is formed by use of a vesicle to which a rare earth metal, such as europium, is chelated. As known in the art, europium may be detected by fluorescence.

The fluorescent rare earth metal, and in particular, europium, as generally known in the art, fluoresces when activated with a suitable activating compound, such as betadiketone or a dihydroxy compound, such as sulfosalicylic acid.

The most widely used B-diketones are benzoylacetone (BA), dibenzoylethane (DBM), thenoyltrifluoroacetone (TTA), benzoyltrifluoroacetone (BTA), 1- and 2- naphthoyltrifluoroacetone (1-/2-NTA), acetylacetone (AcA), trifluoroacetylacetone (TFAcA), and hexafluoroacetylacetone (HFAcA). In addition to B-diketones the lasering properties of different salicylate chelates have previously been investigated and different methods for fluorometric determination of lanthanide ions (Eu, Tb, Sm, Dy) has been developed using these compounds and other ligands, such as terbium with dipicolinic acid (DPA) and with EDTA and sulphosalicylic acid (SSA). Under favorable conditions the quant yield of these chelates can be very high and come close to 100 percent.

The beta-diketone may be provided as a chelate, which chelates the rare earth metal, which is also chelated by the amphiphilic chelating agent employed in producing the vesicle Use of a beta-diketone or other activating compound in this manner is disclosed in U.S. Pat. No. 4,374,120, and such teachings are also applicable to the amphiphilic chelating agents, which are employed in producing a vesicle in accordance with the present invention.

In accordance with a preferred embodiment, the rare earth metal is caused to fluoresce by the use of a suitable activating compound, such as a beta-diketone, after separating the rare earth metal from the chelate.

Thus, for example, a lanthanide, such as europium, may be separated from the amphiphilic chelating agent incorporated into the sac by use of a suitable detergent, such as Triton-X-100 at a low pH value. After separation of the lanthanide, the fluorescence may be amplified by the use of a suitable activating material, such as a beta-diketone. In addition, in order to improve the fluorescence, a Lewis base may be added. Such bases are known, and are generally N-heterocyclic compounds such as o-phenanthroline, phosphines, and phosphine oxides.

Thus, in accordance with a preferred embodiment, the assay is accomplished by employing a fluorescent rare earth metal as the detectable marker, and fluorescence is read by procedures known in the art, with the preferred method being removal of the europium from the chelate, and activation thereof with a beta-diketone, and preferably also a Lewis base.

The assay may be preferably effected by a time delay fluorescent method; however, in some cases, it may be possible to determine fluorescence without a time delay, although a time delay is preferred in that it eliminates background fluorescence. The principles behind a time delay fluorescent assay are known in the art, and such principles are equally applicable to a time delay fluorescent assay in accordance with the present invention wherein the rare earth metal is chelated to a vesicle formed, in part, from an amphiphilic chelating agent, and in part from an amphiphilic compound derivatized with a suitable ligand.

Thus, for example, in such an assay, after separating bound and free components, the europium is removed from the tracer, by use of a detergent, and by addition of a beta-diketone and a Lewis base. The europium is then excited, for example, at 340 nm, and the beta-diketone absorbs energy and transfers the energy to the europium which fluoresces at 614 nm. Fluorescence may be determined in suitable instrumentation available in the art, after a suitable period for permitting decay of background fluorescence, as generally practiced in the art.

Thus, for example, in a typical assay, a vesicle including an amphiphilic chelating agent having europium chelated thereto, and an amphiphilic compound derivatized with a suitable hapten is employed as a tracer in a competitive assay wherein the binder is supported on a solid support such as a test tube. After incubation, the tubes are aspirated, whereby a tube includes only the bound tracer component. Subsequently, a solution containing a beta-diketone, a Lewis base, and a detergent, is added to the tube. The detergent serves the dual purpose of lysing the vesicle, which is bound to the binder on the tube and removing the europium from the chelating agent.

After a time period which permits decay of background fluorescence, fluorescence of the europium is determined on suitable instruentation by excitation at 340 nm, and reading emission at 614. The amount of tracer bound to the tube is inversely proportional to the amount of hapten in the sample, and the quantity may be deterined by the use of a suitable standard curve prepared from standards having known amounts of hapten.

Similarly, tracer in accordance with the present invention may be employed in a "sandwich" type of assay, in wich case, the tracer is formed from a vesicle including an amphiphilic chelating agent having europium chelated thereto, and an amphiphilic compound derivatized with binder for the analyte. The assay may be conducted in a tube coated with a binder for the analyte, and fluorescence determined as hereinabove described. In this type of assay, the amount of tracer which is bound to the tube through the analyte and coated binder is directly proportional to the aount of analyte in the sample.

Thus, in accordance with the present invention, there is provided a dry composition of vesicle forming components in which at least a portion of the components have a detectble marker conjugated thereto (for example, by derivatizing a wall forming compound with a detectable marker such as an enzme or chromogen or by complexing a detectable metal to a chelating agent which is part of the wall forming compound), whereby the vesicle may be reformed by addition of water. As hereinabove indicated, the vesicle is preferably also derivatized with a ligand for use as a tracer in an assay.

In accordance with an embodiment of the present invention, there is provided a reagent kit which includes in an appropriate package a dry mixture of vesicle forming compounds, at least a portion of which are derivatized with a detectable marker and at least a portion of which are derivatized with a ligand. The kit may also include a suitable binder (a binder for the analyte and/or tracer) as well as other materials, such as buffers, standards, promoters activating agents, etc.

The assays which are practiced in accordance with the present invention may be employed in a wide variety of samples; in particular, body fluids such as serum, urine, sputum, etc. The selection of a suitable sample is deemed to be within the scope of those skilled in the art from the teachings herein.

The assay of the present invention may be employed for determining a wide variety of analytes. As representative examples of suitable analytes, there may be mentioned viral antibodies, viral antigen, cardiac glycosides, such as digoxin and digitoxin, various drugs, including therapeutic drugs, and drugs of abuse, hormones, such as $T_4$, $T_3$ hCG, TSH, various steroids, and the like. These and other analytes should be apparent to those skilled in the art from the teachings herein and no further teachings in this respect are deemed necessary for a full understanding of the invention.

The invention will be further described with respect to the following examples; however, the scope of the invention is not to be limited thereby:

EXAMPLES

A. Synthesis of Diethylenetriaminopentaacetic Acid-Dioctyldecylamine (DIPH-DODA)

The bis-anhydride of DTPA was prepared by refluxing DTPA (100 mmol, 38.5 gm) in 120 ml of 1:1 v/v pyridine and acetic anhydride under a $N_2$ atmosphere for 18 hours. The solid was filtered, washed with acetic acid anhydride and then washed with ether. The material was dried in a vacuum oven overnight at 125° C. and 70 microns. The yield was 95% (36 gm).

The typical synthetic procedure for (DTPA-DODA) was devised by modification of Takeshita's protocol (JAOCS 59, No. 2, February, 1982, 104–107). DTPA bis-anhydride (30 mmol, 11 gm) and triethylamine (20 mmol, 2.02 gm) were suspended in 50 ml of tetrahydrofuran (THF) under a $N_2$ atmosphere and heated to 50° C. The DODA (5 mmol, 2.65 gm) was dissolved in 10 ml of THF and added through an addition funnel over 1 hr. The solution was stirred overnight. After being cooled, the mixture was poured into a large excess of water (200 ml) and filtered. The residue was washed with water to give the crude product. The crude product was dissolved in aqueous sodium hydroxide (120 ml) at pH 10. The solution was shaken with ether $2\times(100$ ml). The ethereal and emulsified phases containing unreacted amine were discarded. The water phase was neutralized with 10% HCl. The dissolved ether was removed by rotary evaporation. The solution was adjusted to pH 4 with 10% HCl to yield a precipitate. The precipitate was separated, washed with distilled water and dried for 5 hours at 80° C. under vacuum. The dried material was recrystallized from ethanol and water. The material was characterized by TLC, IR, and NMR. The yield was 15% (600 mg).

B. Preparation of Digoxin-Labeled Europium-Bound Liposomes

Europium binding liposomes were prepared by placing 132 umole cholesterol, 119 umole distearoyl phosphatidylcholine, 13.2 umole distearoyl phosphatidylglycerol, 0.2 umole distearoyl phosphatidylethanolamine-digoxin conjugate and 62 umole diethylenetriaminopentaacetic acid-dioctyldecylamino conjugate in 20 ml of chloroform-methanol (9:1 v/v). After evaporation of the organic solvents, the remaining lipids were resuspended in 50 ml Tris buffer (Trimza Base 50 umole, NaCl 117 umole, pH 8.0) containing 31 umole $Eu(NO_3)_3$. This suspension was sonicated for 20 minutes at 100 watts (4 C) and then centrifuged at 2,000 rpm for 5 min. The supernate was passed over a PD-10 gel filtration column and the liposome fraction collected in the void volume. These liposoxes were 200 nm in size as determined with the Coult ®r Particle Analyzer Model N4. The liposomes were lyophilized and reconstituted in the Tris buffer. The size distribution profiles before and after lyophilization were very similar. Three separate batches of liposomes were prepared in this manner.

C. Assays Utilizing Digoxin-Labeled Europium-Bound Liposomes

A heterogeneous competition assay was developed using the previously prepared DTPA-DODA liposomes, anti-digoxin coated tubes and serum standards of digoxin (BDI, Orangeburg). To the anti-digoxin coated tubes were added 50 ul of digoxin serum standards (0–10 ng/ml), 50 ul of liposomes, and 900 ul of Tris buffer. After incubation for 45 minutes at 37oC, the tubes were aspirated and washed. Two ml of a solution containing $10^{-5}M$ napthylenetrifluoroacetylacetonate, $10^{31\ 5}$ tri-N-octylphosphine oxide, 0.1% Triton X-100, 0.5% acetic acid, and 2% ethanol was added to each tube. The tima-resolved fluorescence was determined after 10 minutes utilizing a Spex L-111 instrument and the following optimized parameters, 100 flashes per data point, excitation 340 nm, emission at 614 nm, 0.5 ms delay, 0.25 ms window, and four slits of 0/0/.5/.5 mm. Seven different concentrations of digoxin serum standards were tested, and all samples were run in duplicate. A calibration curve was constructed.

D. Synthesis of Diethylenetriaminopentaacetic Acid - Diaminohexane-Cholesterol (DTPA-DAH-Chol)

The typical synthetic procedure for (DAH-Chol) was devised by modification of Rando's protocol (*Biochimica et Biophysica Acta*, 684 (1982) 12–20). Diaminohexane (DAH), 26 mmol, 3.1 gm) and triethylamine (26 mmol, 2.67 gm) were dissolved in isopropanol (75 ml). With stirring, beta cholesterol chloformate (9 mmol, 4.05 gm) in benzene (9 ml), was added over 1 hr. After stirring overnight, the suspension was filtered and the filtrate taken to dryness. The solid precipitate was dissolved in methylene chloride and extracted once with 10% $Na_2CO_2$ and five times with saturated sodium chloride. The organic layer was dried over sodium sulfate and taken to dryness. The solid was recyrstallized from methanol. The material was characterized by TLC and IR. The yield was 65% (3.6 gm).

The typical synthetic procedure for (DTPA-DAH-Chol) was devised by modification of Takeshita's protocol (*JAOCS* 59 No. 2, February, 1982, 104–107). DTPA bis-anhydride (29 mmol, 7.2 gm) and triethylamine (33 mmol, 3.36 gm) were suspended in tetrahydrofuran (THF) (50 ml) under a N2 atmosphere and heated to 50° C. The DAH-Chol (4 mmol, 2.3 gm) was dissolved in THF (10 ml) and added through an addition funnel over 1 hr. The solution was stirred overnight. After being cooled, the mixture was poured into a large excess of water and filtered. The residue was washed with water to give the crude product. The crude product (2.5 gm) was dissolved in $CH_2Cl_2$:MeOH:AcOH (20:4:0.1 v/v) and applied to a LS-2 silica gel column equilibrated with the same solvent system. The product was purified by flash chromatography. The product eluted between 1,400–2,200 ml of solvent, and those fractions were pooled and evaporated. The material was characterized by TLC and IR. The yield was 45% (1.75 gm).

E. Preparation of Digoxin-Labeled Europium-Bound Liposomes

Europium binding liposomes were prepared by placing 77 umole DTPA-DAH-Chol, 119 umole distearoyl phosphatidylcholine, 13.2 umole distearoyl phosphatidylglycerol, and 0.2 umole distearoyl phosphatidylethanolamine-digoxin conjugate in 20 ml of chloroform-methanol (9:1 v/v). After evaporation of the organic solvents, the remaining lipids were resuspended in 50 ml Tris buffer (Trimza Base 50 umole, NaCl 117 umole, pH 8.0) containing 31 umole Eu(-$NO_3)_3$. This suspension was sonicated for 20 minutes at 100 watts (4° C.) and then centrifuged at 2,000 rpm for 5 min. The supernate was passed over a PD-10 gel filtration column and the liposome fraction collected in the void volume. These liposomes were 200 nm in size as determined with the Coulter Particle Analyzer Mcdel N4. The liposomes were lyophilized and reconstituted in the Tris buffer. The size distribution profiles before and after lyophilization were very similar. Three separate batches of liposomes were prepared in this manner.

F. Assays Utilizing Digoxin-Labeled Europium-Bound Liposomes

A heterogeneous competition assay was developed using the previously prepared DTPA-DAH-Chol liposomes, anti-digoxin coated tubes and serum standards of digoxin (BDI, Orangeburg). To the anti-digoxin coated tubes were added 50 ul of digoxin serum standards (0–10 ng/ml), 50 ul of liposomes, and 900 ul of Tris buffer. After incubation for 45 minutes at 37° C., the tubes were aspirated and washed. Two ml of a solution containing $10^{-5}$ M napthylenetrifluoroacetylacetonate, $10^{-5}$ tri-N-octylphosphine oxide, 0.1% Triton X-100, 0.5% acetic acid, and 2% ethanol was added to each tube. The tie-resolved fluorescence was determined after 10 minutes utilizing a Spex L-111 instrument and the following optimized parameters, 100 flashes per data point, excitation 340 nm, emission 614 nm, 0.5 ms delay, 0.25 ms window and four slits of 0/0/.5/.5 mm. Seven different concentrations of digoxin serum standards were tested, and all samples were run in duplicate. A calibration curve was constructed.

The present invention is particularly advantageous in that it is possible to provide all the advantages associated with the use of vesicles including a detectable marker, while eliminating the storage problems heretofore encountered as a result of storing the vesicles in water.

These and other advantages should be apparent to those skilled in the art from the teachings herein.

What is claimed is:

1. A composition comprising: a dry mixture of vesicle wall forming amphiphilic compounds, at least a portion of said compounds being a vesicle wall forming amphiphilic chelating agent, having a detectable metal atom complexed therewith.

2. The composition of claim 1 wherein at least a portion of the wall forming compounds have a ligand conjugated thereto.

3. The composition of claim 1 wherein the dry mixture is produced by drying of a vesicle.

4. The composition of claim 1 wherein a further portion of said vesicle is formed from an amphiphilic compound derivatized with a ligand.

5. The composition of claim 4 wherein the detectable metal atoms are comprised of fluorescent rare earth metal.

6. The composition of claim 4 wherein the chelating portion of the amphiphilic chelating agent is comprised of a diethylenetriaminepentaacetic acid.

7. The composition of claim 6 wherein the hydrophobic portion of the amphiphilic chelating agent is comprised of a dialkyl amine.

8. The composition of claim 7 wherein the detectable metal atoms are comprised of fluorescent rare earth metal.

9. The composition of claim 6 wherein the hydrophobic portion of the amphiphilic chelating agent is comprised of cholesterol.

* * * * *